US010789424B2

(12) United States Patent
Galassi

(10) Patent No.: US 10,789,424 B2
(45) Date of Patent: Sep. 29, 2020

(54) SYSTEM AND METHOD FOR MULTI-DIMENSIONAL KNOWLEDGE REPRESENTATION

(71) Applicant: Christopher R. Galassi, Schaumburg, IL (US)

(72) Inventor: Christopher R. Galassi, Schaumburg, IL (US)

(73) Assignee: Christopher R. Galassi, Schaumburg, IL (US)

( * ) Notice: Subject to any disclaimer, the term of this patent is extended or adjusted under 35 U.S.C. 154(b) by 0 days.

(21) Appl. No.: 16/299,651

(22) Filed: Mar. 12, 2019

(65) Prior Publication Data

US 2019/0370318 A1   Dec. 5, 2019

Related U.S. Application Data

(63) Continuation of application No. 13/813,932, filed as application No. PCT/US2011/046804 on Aug. 5, 2011, now abandoned.

(60) Provisional application No. 61/370,955, filed on Aug. 5, 2010.

(51) Int. Cl.
  *G06F 17/00* (2019.01)
  *G06F 40/197* (2020.01)
  *G06F 40/131* (2020.01)

(52) U.S. Cl.
  CPC .......... *G06F 40/197* (2020.01); *G06F 40/131* (2020.01)

(58) Field of Classification Search
  CPC ................................................... G06F 17/2229
  See application file for complete search history.

(56) References Cited

U.S. PATENT DOCUMENTS

| 4,787,038 A | 11/1988 | Doi et al. |
| 5,655,130 A | 8/1997 | Dodge et al. |
| 6,236,409 B1 | 5/2001 | Hartman |
| 6,683,611 B1 | 1/2004 | Cleveland |
| 7,548,910 B1 | 6/2009 | Chu et al. |
| 2003/0018481 A1* | 1/2003 | Zhou ................ G06Q 50/18 715/223 |
| 2004/0181390 A1 | 9/2004 | Manson |
| 2005/0021322 A1 | 1/2005 | Richardson et al. |
| 2005/0071755 A1 | 3/2005 | Harrington et al. |
| 2005/0278623 A1 | 12/2005 | Dehlinger et al. |
| 2006/0069986 A1 | 3/2006 | Sandoval |
| 2006/0190815 A1 | 8/2006 | Jones et al. |
| 2007/0130563 A1 | 6/2007 | Elgazzar et al. |
| 2009/0024613 A1 | 1/2009 | Niu et al. |
| 2009/0070094 A1 | 3/2009 | Best et al. |
| 2010/0058169 A1 | 3/2010 | Demant et al. |
| 2010/0100817 A1 | 4/2010 | Trotter |
| 2012/0324350 A1 | 12/2012 | Rosenblum et al. |
| 2014/0047327 A1 | 2/2014 | Larsen et al. |

* cited by examiner

*Primary Examiner* — Scott T Baderman
*Assistant Examiner* — Barbara M Level
(74) *Attorney, Agent, or Firm* — McDonnell Boehnen Hulbert & Berghoff LLP

(57) ABSTRACT

Exemplary embodiments generally relate to knowledge representation, and in particular, multi-dimensional knowledge representation in a configurable document that includes a collection of subparts that have a number of dimensions. Further, a number of versions of each configurable document may be defined, with each version including a different subset of subparts from the collection of subparts.

20 Claims, 10 Drawing Sheets

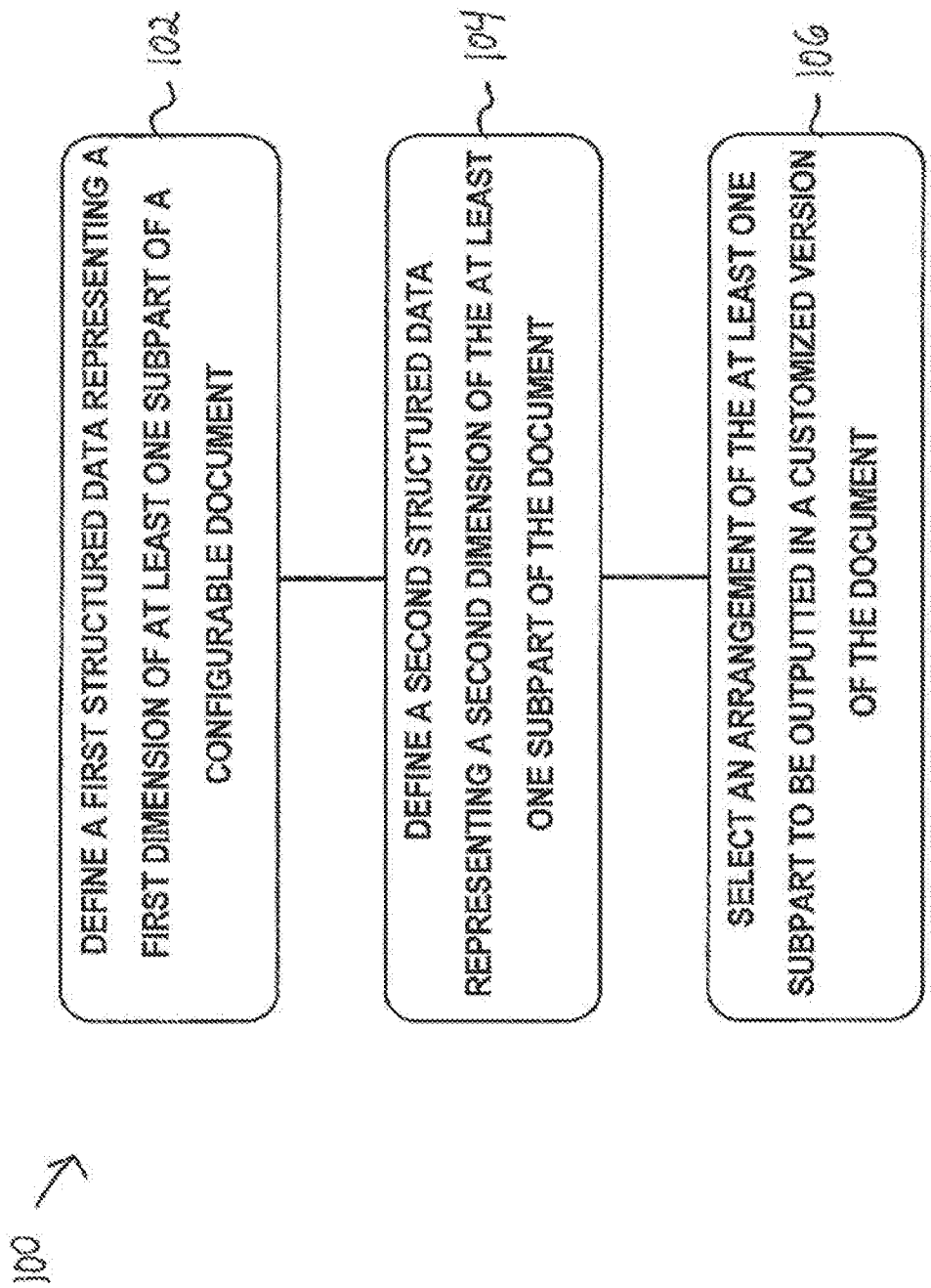

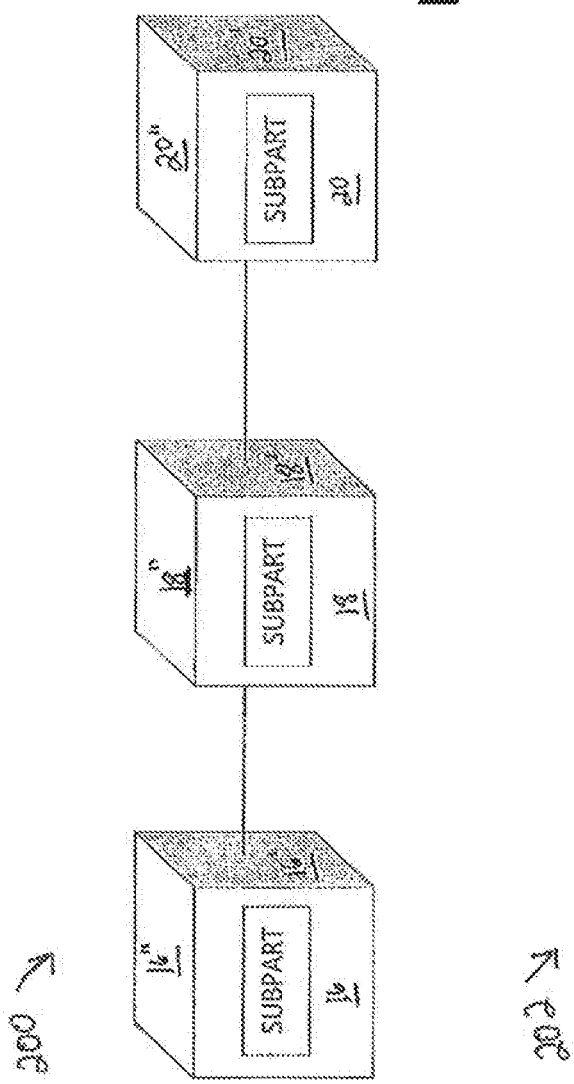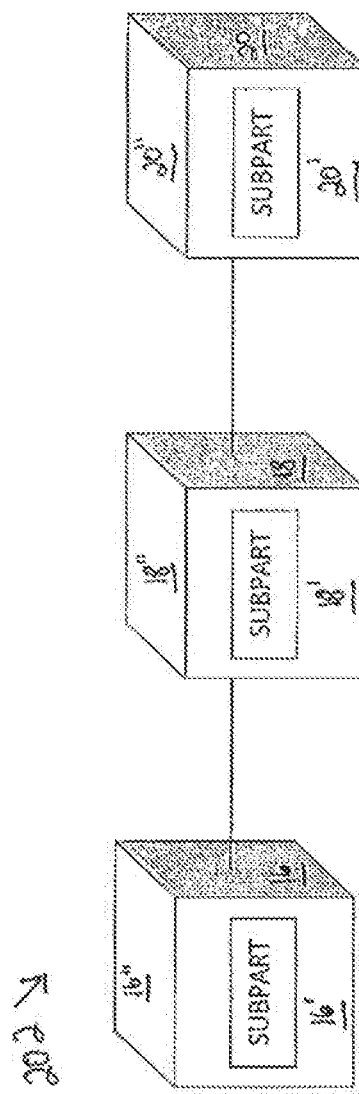

SYSTEM AND METHOD FOR MULTI-DIMENSIONAL KNOWLEDGE REPRESENTATION

RELATED APPLICATION

This application is a continuation of U.S. patent application Ser. No. 13/813,932, filed Feb. 13, 2013, which claims priority to PCT Application No. PCT/US2011/046804, filed Aug. 5, 2011, which claims priority to U.S. Provisional Application No. 61/370,955, filed Aug. 5, 2010, all of which are incorporated by reference herein for all purposes.

FIELD OF THE INVENTION

The present invention relates generally to knowledge representation. In particular, the invention is directed to a system and a method for multi-dimensional knowledge representation in a configurable document that includes a number of subparts that have a number of dimensions.

BACKGROUND

Unless otherwise indicated herein, the materials described in this section are not prior art to the claims in this application and are not admitted to be prior art by inclusion in this section.

In the specialized domain of medicine, it is frequently important for a healthcare worker to provide a customized version of instructions to patients, for example at the time of discharge. When the healthcare provider does not speak the language of the patient, it is not possible for her to compose a customized version of a set of discharge instructions in the language of the patient. Furthermore, with the overwhelming overcrowding of American healthcare facilities, increases in throughput are an institutional imperative and any means to provide customized instructions in a time-efficient manner is a critical quality improvement.

There is currently no solution to allow accurate, fast, and reliable customization or translation of documents to a foreign language for non-foreign language speakers. The use of medical translators for creation of custom foreign language written instructions is vastly impractical. The expense of such staff and delays incurred in patient care and discharge would be substantial.

There are some computer programs for automatic language translation by computers but they do not provide accurate translations. The output of such systems is often dangerously inaccurate and even nonsensical. This is particularly true and problematic in specialized domains such as in medicine, which often includes specialized patient instructions, wherein a critical insight is needed for accurate translations.

For example, consider an individual having a "felon on their finger", (a medical condition). An automatic Spanish translation of such text would result in a translated text stating a patient had the English equivalent of a "criminal" on their finger. Such inaccuracies are dangerously prohibitive for use with patient care, and may similarly have negative repercussions in other scenarios and/or contexts.

SUMMARY

In the vast majority of medical-related cases, a conventional document system is rudimentary and does not have the ability to provide customization in various languages or visual representations. The need for an easily configurable document system is evidenced in that virtually all electronic healthcare systems that provide for the treatment of patients include some form of patient written information for dispensing to the patient.

It would therefore be desirable to develop a system and a method for knowledge representation that allows a user to selectively output alternative views or versions of a configurable document in a time-efficient manner.

Concordant and consistent with the present invention, a system and a method for knowledge representation that allow a user to selectively output alternative views or versions of a configurable document in a time-efficient manner, has surprisingly been discovered.

In one embodiment, a system for knowledge representation comprises: a configurable document having a structured data divided into at least one subpart, wherein the subpart has a pre-determined number of data dimensions associated therewith; and an editing interface in data communication with the document to modify the structured data of the at least one subpart.

Exemplary embodiments may also provide methods for knowledge representation. One method comprises the steps of: defining a first structured data representing a first dimension of at least one subpart of a configurable document; defining a second structured data representing a second dimension of the at least one subpart of the document; and selecting an arrangement of the at least one subpart to be outputted in a customized version of the document.

In another aspect, an exemplary computer-implemented method may involve: (i) causing a graphic display to display an editing interface for creating a configurable document, wherein the configurable document comprises a collection of subparts, and wherein one or more of the subparts comprises a plurality of dimensions; (ii) receiving, via the editing interface, data specifying a collection of subparts to include in the collection of subparts; (iii) receiving, via the editing interface, data specifying a plurality of dimensions for each indicated subpart; (iv) generating and storing a configurable document comprising the specified collection of subparts, wherein each of the subparts comprises the respectively specified plurality of dimensions; (v) storing the configurable document comprising the specified plurality of dimensions for each subpart in the specified collection of subparts; (vi) receiving two or more version-creation instruction via the editing interface, wherein each version-creation instructions comprises an indication of a subset of the collection of subparts; and (vii) storing two or more predefined versions of the configurable document, wherein each predefined version comprises a different subset of subparts from the collection of subparts.

In another aspect, an exemplary embodiment may take the form of a non-transitory computer-readable medium having instructions stored thereon, the instructions including: (i) instructions for causing a graphic display to display an editing interface for creating a configurable document, wherein the configurable document comprises a collection of subparts, and wherein one or more of the subparts comprises a plurality of dimensions; (ii) instructions for receiving, via the editing interface, data specifying a collection of subparts to include in the collection of subparts; (iii) instructions for receiving, via the editing interface, data specifying a plurality of dimensions for one or more of the indicated subparts; (iv) instructions for generating and storing a configurable document comprising the specified collection of subparts, wherein each of the subparts comprises the respectively specified plurality of dimensions; (v) instructions for storing the configurable document comprising the specified plurality of dimensions for each subpart in the specified collection of subparts; (vi) instructions for receiving two or more version-creation instruction via the editing interface, wherein each version-creation instructions comprises an indication of a subset of the collection of subparts, (vii) instructions for storing two or more predefined versions of the configurable document, wherein each predefined version comprises a different subset of subparts from the collection of subparts.

In another aspect, an exemplary computer-implemented method may involve: (i) causing a graphic display to display an editing interface for creating a custom version of a configurable document, wherein the configurable document comprises a collection of subparts, wherein one or more of the subparts comprises a plurality of dimensions, wherein the editing interface provides for selection of a particular predefined version of the configurable document from a plurality of predefined versions of the configurable document, and wherein each predefined version comprises a subset of the collection of subparts; (ii) receiving a version-selection instruction via editing interface, wherein the version-selection instruction indicates a selected predefined version of the configurable document from the plurality of predefined versions; (iii) in response to the version-selection instruction, causing the graphic display to display the collection of subparts in the editing interface, and to visually indicate in the editing interface which subparts from the collection are included in the selected predefined version; (iv) receiving one or more sub-part selection instructions via the editing interface, wherein each sub-part selection instruction indicates to select or de-select an individual subpart from the collection of subparts; (v) receiving one or more dimension-selection instructions via the editing interface, wherein each dimension-selection instruction indicates to select a particular dimension for one or more of the selected subparts; and (vi) receiving a document-generation instruction and responsively generating a custom version of the configurable document, wherein the custom version comprises the selected dimension for each of the one or more subparts that are selected in the editing interface.

In another aspect, an exemplary embodiment may take the form of a non-transitory computer-readable medium having instructions stored thereon, the instructions including: (i) instructions for causing a graphic display to display an editing interface for creating a custom version of a configurable document, wherein the configurable document comprises a collection of subparts, wherein one or more of the subparts comprises a plurality of dimensions; and wherein the editing interface provides for selection of a particular predefined version of the configurable document from a plurality of predefined versions of the configurable document, wherein each predefined version comprises a subset of the collection of subparts and a particular dimension for each subpart in the subset; (ii) instructions for receiving a version-selection instruction via editing interface, wherein the version-selection instruction indicates a selected predefined version of the configurable document from the plurality of predefined versions; (iii) instructions for, in response to the version-selection instruction, causing the graphic display to display the collection of subparts in the editing interface, and to visually indicate in the editing interface which subparts from the collection are included in the selected predefined version; (iv) instructions for receiving one or more sub-part selection instructions via the editing interface, wherein each sub-part selection instruction indicates to select or de-select an individual subpart from the collection of subparts; (v) instructions for receiving one or more dimension-selection instructions via the editing interface, wherein each dimension-selection instruction indicates to select a particular dimension for one or more of the selected subparts; and (vi) instructions for receiving a document-generation instruction and responsively generating a custom version of the configurable document, wherein the custom version comprises the selected dimension for each of the one or more subparts that are selected in the editing interface.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

The above, as well as other advantages of the present invention, will become readily apparent to those skilled in the art from the following detailed description of the preferred embodiment when considered in the light of the accompanying drawings in which:

FIG. 2 is a schematic flow diagram of a method for knowledge representation according to an embodiment of the present invention;

FIG. 3A is a schematic representation of a first view or arrangement of a structured data according to an embodiment of the present invention; and FIG. 3B is a schematic representation of a second view or arrangement of the structured data of FIG. 3A.

FIG. 6A is an illustration of a screen from an editing interface in a medical application, according to an exemplary embodiment FIG. 7A is an illustration of another screen from an editing interface in a medical application, according to an exemplary embodiment

DETAILED DESCRIPTION

The following detailed description and appended drawings describe and illustrate various exemplary embodiments of the invention. The description and drawings serve to enable one skilled in the art to make and use the invention, and are not intended to limit the scope of the invention in any manner, which is defined by the claims. It will be readily understood that certain aspects of the disclosed systems and methods can be arranged and combined in a wide variety of different configurations, all of which are contemplated herein. In respect of the methods disclosed, the steps presented are exemplary in nature, and thus, the order of the steps is not necessary or critical. Further, it should be understood that the word "exemplary" is used herein to mean "serving as an example, instance, or illustration." Any embodiment or feature described herein as "exemplary" is not necessarily to be construed as preferred or advantageous over other embodiments or features.

Figure 1:
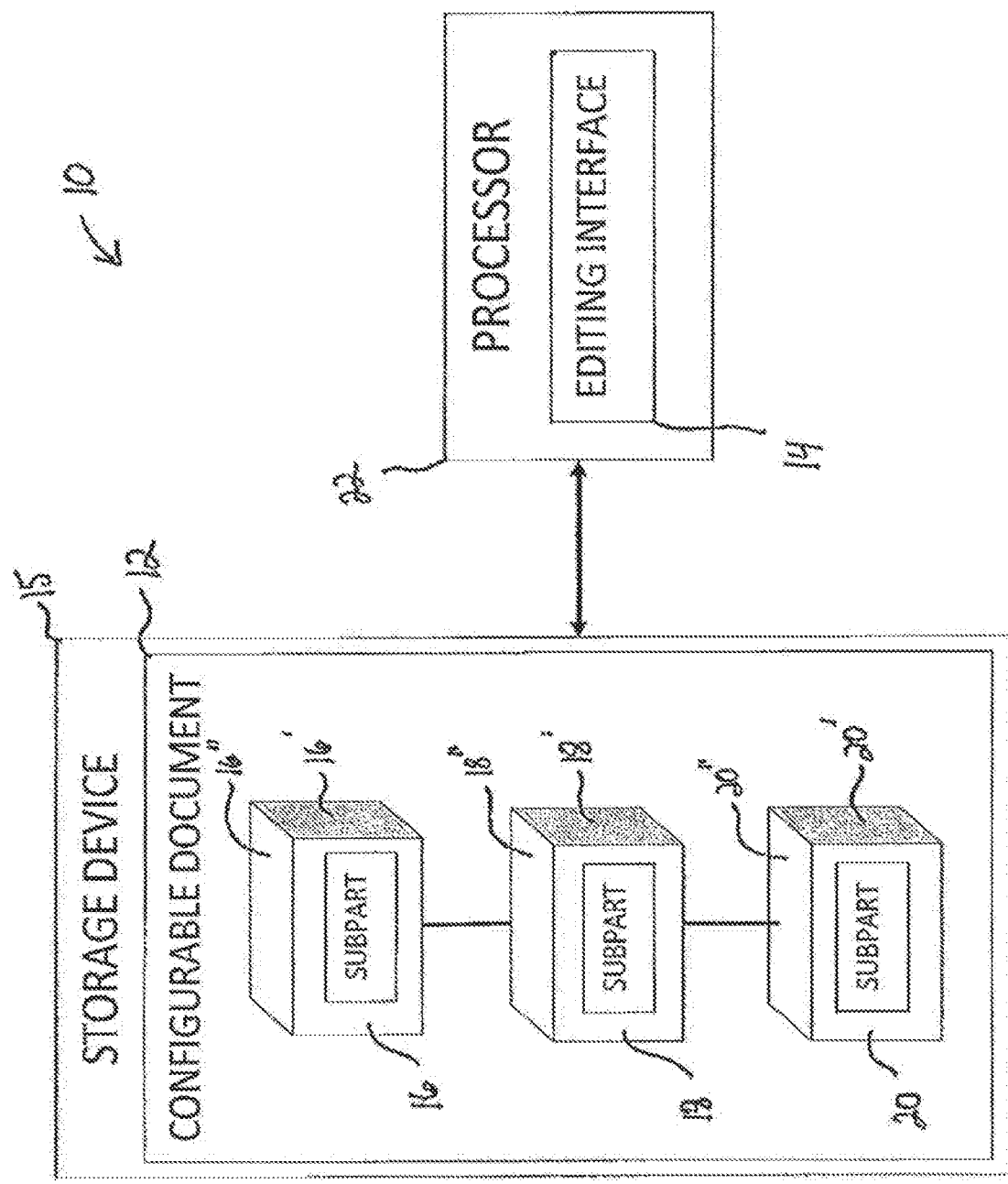
FIG. 1 is a schematic block diagram of a system for knowledge representation according to an embodiment of the present invention.

Referring now to FIG. 1, there is illustrated a multi-dimensional knowledge representation system, indicated generally at 10. The system 10 includes a configurable, multi-dimensional configurable document and an editing interface 14 for manipulation and use of the configurable document 12.

The configurable document includes a structured document data (e.g. knowledge representation) that allows a single document to be represented with alternative views (e.g. alternative languages, text, graphics, etc.). The configurable document is typically created and stored in a computer environment on a non-transitory computer-readable medium. Specifically, the structured data of the configurable document may be stored in a data storage device 15.

The structured data of the configurable document is divided into subparts 16, 18, 20, wherein at least one of the subparts 16, 18, 20 of the configurable document is selectively arranged to create one of a plurality of alternative views (i.e. customized versions) of the configurable document. It is understood that any number of the subparts 16, 18, 20 can be created or defined. It is further understood that each of the subparts 16, 18, 20 can include any amount of data representing any portion of the configurable document (e.g. a letter, a word, a paragraph, a graphic, etc.).

In some embodiments, each subpart 16, 18, 20 of the configurable document may correspond to a "knowledge chunk" that conveys a certain piece of knowledge or a certain concept. Further, each dimension of a given subpart may be a different representation of the same knowledge chunk. For examples, different dimensions of a given subpart may take the form of, for example, different textual or graphical representations of the piece knowledge provided by the knowledge chunk.

The subparts 16, 18, 20 can be further hierarchically structured to an arbitrary depth to allow automatic inclusion of one of the subparts 16, 18, 20 when a related one of the subparts 16, 18, 20 is selected to be outputted. For example, the configurable document can be structured to automatically select the subpart 20 any time a user selects the subpart 16. It is understood that any relationship between the subparts 16, 18, 20 can be defined. It is further understood that the subparts 16, 18, 20 can be configured in any arrangement including any number of the subparts 16, 18, 20.

The configurable document further includes a data structure that allows additional dimensions of "configuration" so that uniquely composed named versions of the configurable document can be saved within its structure and retrieved for output regardless of the view selected for output. As a non-limiting example, each of the subparts 16, 18, 20 in a first dimension is shown having a reciprocal subpart 16', 18', 20' in a second dimension, and a reciprocal subpart 16", 18", 20" in a third dimension. It is understood that any of the subparts 16, 16', 16", 18, 18', 18", 20, 20', 20" can represent any portion of the configurable document such as a paragraph of written text, a translation of the paragraph of written text into a pre-defined language, a graphical representation of the paragraph of written text, etc.).

It is understood that a software implementation of the system 10 can take many forms. Data can be stored in tables with the relationship between the subparts 16, 16', 16", 18, 18', 18", 20, 20', 20" captured in traditional relational table models. As a non-limiting example, the data structure of the configurable document and the subparts 16, 16', 16", 18, 18', 18", 20, 20', 20" can be stored in a single file format using a definition of a tagged data structure. It is further understood that the data format can include a particular grammatical structure, yet encoded using any conventional file structuring formats such as rich text format (RTF) or extensible markup language (XML). Additionally, traditional mechanisms of format encoding for bold and textual font or highlighting mechanisms can be included in the subparts 16, 16', 16", 18, 18% 18", 20, 20', 20" to more closely approximate full text editing.

In a further aspect, an exemplary system may take the form of a non-transitory computer readable medium, which has instructions for accessing a library of configurable documents. In some embodiments, the library of configurable documents, and both predefined and custom versions of the configurable documents, may be stored in a serialized form in a database (e.g., a SQL database). Further, the system may provide an editing interface, such as that described herein, which allows a user to: (a) author new configurable documents to add to the library, (b) load a predefined version of a configurable document from the library, select a dimension for the predefined version, and output a flattened or "one-dimensional" document from the predefined version (which may be set by default or may be selected by the user), (c) load a predefined version of a configurable document from the library, edit and/or arrange the subparts of the predefined version to create a custom version, and then out output a flattened or "one-dimensional" document from the custom version, among other functions.

The editing interface 14 may be similar to a conventional text editor. The editing interface 14 is typically embodied as an instruction set (i.e. software code) executable by a processor 22 to allow the user to create, review, modify, store, retrieve, and output any number of the documents 12. In particular, the editing interface 14 provides a means for the user to access the configurable document and select an arrangement of the subparts 16, 16', 16", 18, 18', 18", 20, 20', 20" to create a composed custom version of the configurable document. The user can view the configurable document in expanded or collapsed format (i.e. view selected or all of the subparts 16, 16', 16", 18, 18% 18", 20, 20% 20"), view an alternative arrangement of the subparts 16, 16', 16", 18, 18% 18", 20, 20', 20", or view a split screen format showing both the composed custom version of the configurable document and an alternative view for comparison. The editing interface 14 allows particular configurations of the subparts 16, 16', 16", 18, 18', 18", 20, 20', 20" to be saved as named configurations to allow fast access on subsequent use. The named configurations are available to view or output using one or more of the views (e.g. translation) to provide customized output (eg. multi-lingual) of the document. Any view or views of the configurable document can be selected and outputted in a plain text format to yield one or more standard documents.

FIG. 2 illustrates a method 100 for knowledge representation that can be executed using the system 10. In step 102, a structured data is defined, the structured data representing a first dimension of at least one of the subparts 16, 18, 20 of the configurable document. As a non-limiting example, the subparts 16, 18, 20 in the first dimension are created manually based on a user-provided input. However, other means of creating or defining the data associated with the subparts 16, 18, 20 of the first dimension can be used.

In step 104, a structured data representing the subparts 16', 18', 20' in the second dimension are defined. As a non-limiting example, the subparts 16', 18', 20' in the second dimension can also be created manually by a user. The user can also create a rule to automatically generate the subparts 16', 18', 20' in the second dimension based upon the data representing the subparts 16, 18, 20 in the first dimension. As a non-limiting example, the user can create a rule to automatically translate the data representing the subparts 16, 18, 20 into a pre-defined first language and store the translated data as the subparts 16', 18', 20' in the second dimension. As a further non-limiting example, the user can create a rule to automatically translate the data representing the subparts 16, 18, 20 into a pre-defined second language and store the translated data as the subparts 16", 18", 20" in the third dimension. As a further non-limiting example, the user can create a rule to automatically manipulate the data representing the subparts 16, 18, 20 into a graphical representation and store the graphical representation as the subparts 16', 18', 20' in the second dimension. It is understood that any rule can be created to manipulate the data from one of the dimensions and store a reciprocal data in another dimension. It is further understood that each of the subparts 16, 16', 16", 18, 18', 18", 20, 20', 20" in any dimension can be manually created.

In step 106, the user selects an arrangement of at least one of the subparts 16, 16', 16", 18, 18', 18", 20, 20' (including any of the pre-defined dimensions) to be outputted in a customized version or view of the document.

As an illustrative example, FIG. 3A shows a first view 200 or arrangement of a structured data, wherein at output based on the first view 200 includes a configuration of the subparts 16, 18, 20. As shown, the subparts 16, 18, 20 are arranged in a specific sequential order representing a physical layout of the associated visible information (e.g. text, graphics, etc.). It is understood that the subparts 16, 18, 20 in the first view 200 may correspond to alternative subparts 16', 16", 18', 18", 20', 20" in an alternative view.

As a further illustrative example, FIG. 3B shows a second view 202 or arrangement of a structured data, wherein an output based on the second view 202 includes a configuration of the subparts 16', 18', 20'. As shown, the subparts 16', 18', 20' are arranged in a specific sequential order representing a physical layout of the associated visible information (e.g. text, graphics, etc.). It is understood that the subparts 16', 18', 20' in the second view 202 may correspond to alternative subparts 16, 16", 18, 18", 20, 20" in an alternative view.

It is understood that the views 200, 202 of the configurable document correspond to various arrangement of the underlying structured data of the configurable document. As a non-limiting example, the multi-dimensional configurable document can have alternative views or versions presenting the same base information in various languages. As a further example, a particular data can be represented in the configurable document as a picture, a graph, or a table in a particular view. Any number of alternative views can be generated by various arrangements of the structured data in multiple pre-defined dimensions.

The system 10 and the method 100 provide a means for non-foreign language speaking individuals to create a customized version of standard instructions in virtually any foreign language. The system 10 and method 100 have potentially broad applicability and a particular immediate use in the medical domain to allow non-foreign language speaking healthcare providers to create customized written patient discharge instructions.

In certain embodiments described herein, exemplary methods and systems may be described as being applied in a healthcare environment. As a non-limiting example, the quickly customizable multi-dimensional configurable document can be used in a wide variety of healthcare settings. In many instances, medicine involves a domain of "standard of care" treatment-specific responses and standard patient documents, such as during a patient discharge process, for example. Other examples in a healthcare environment are also possible.

Further, examples in many other environments are also possible. For instance, beyond the medical domain, exemplary embodiments can be applied to applications in law, government, and public dissemination of information for any setting in which one individual needs to provide customized information to another. Some of the many settings in which exemplary embodiments may be applicable include the hospital Emergency Department, Inpatient Facilities, Clinics, Offices, Public Health Facilities, School Wellness Facilities, Center for Disease Control, the Department of Homeland Security, a bioterrorism preparedness center, and many others, for example.

Methods for Creating a Configurable Document

As noted above, an exemplary embodiment may involve an editing interface that allows for creation of a configurable document. With such an editing interface, a user may define subparts for a configurable document, as well as dimensions for each subpart.

Figure 4:
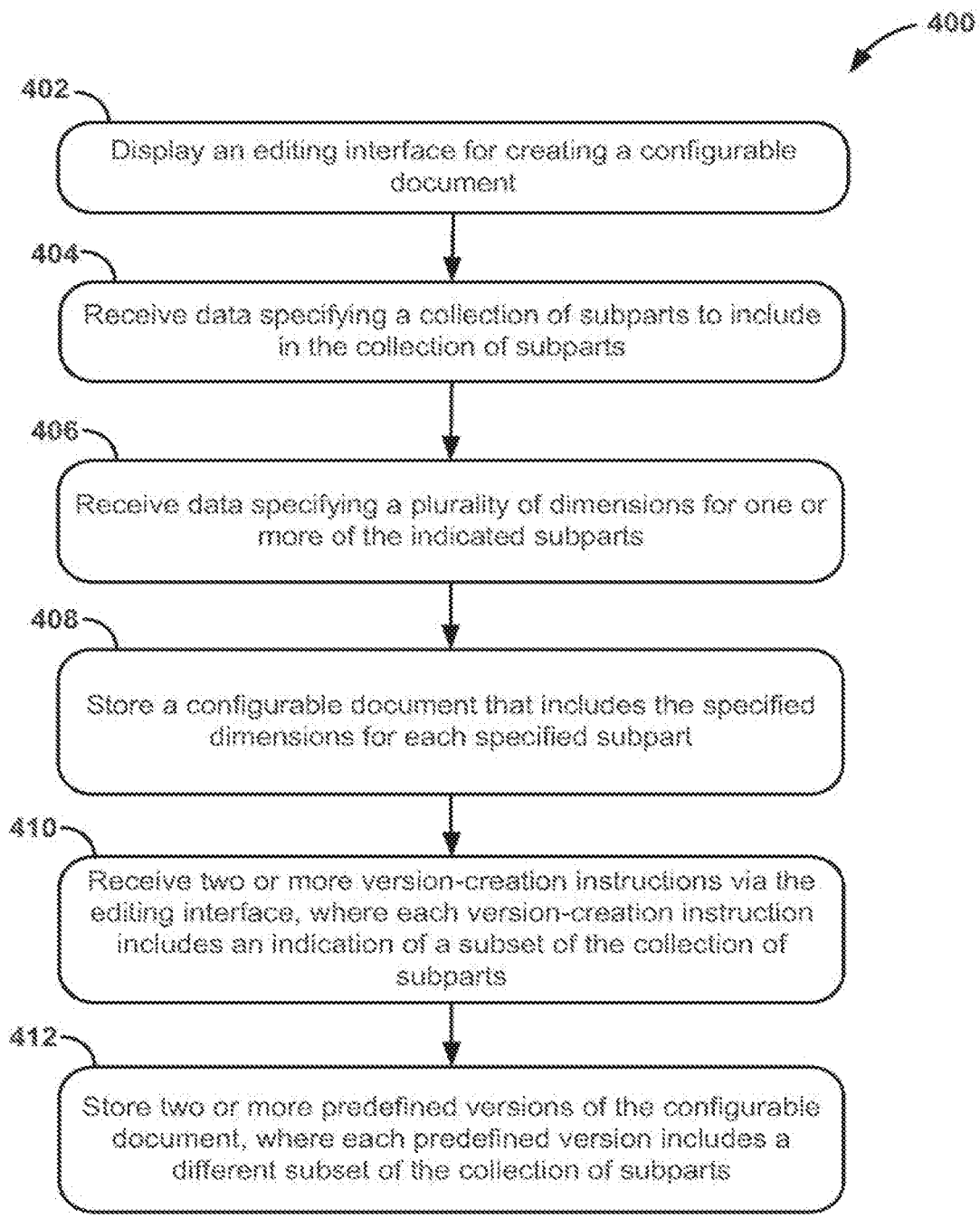
FIG. 4 is a flow chart illustrating a method, according to an exemplary embodiment.

FIG. 4 is a flow chart illustrating a method 400, according to an exemplary embodiment. Method 400 may be implemented by a computing device to provide an editing interface for creating a configurable document, to receive data via the editing interface, and to generate and store a configurable document based on the received data.

More specifically, method 400 involves the computing device causing a graphic display to display an editing interface for creating a configurable document, which includes a collection of subparts, with one or more of the subparts having a plurality of dimensions, as shown by block 402. The computing device then receives data for the configurable document via the editing interface. In particular, the computing device may receive data specifying a collection of subparts to include in the collection of subparts, as shown by block 404. The computing device may then receive data specifying a plurality of dimensions for one or more of the indicated subparts, as shown by block 406. The computing device then generates and stores a configurable document that includes the specified dimensions for each specified subpart, as shown by block 408.

In some embodiments, exemplary method 400 may be used to create a configurable document in which each of the subparts corresponds to a particular knowledge chunk, and in which each dimension of a given subpart is a different representation of the corresponding knowledge chunk. In such an embodiment, the provided editing interface may allow a user to specify the knowledge chunks to include in the configurable document. The editing interface may further allow a user to specify the various representations of each knowledge chunk.

As further shown in FIG. 4, method 400 involves the computing device receiving two or more version-creation instructions via the editing interface, where each version-creation instruction includes an indication of a subset of the collection of subparts, as shown by block 410. The computing device may then store two or more predefined versions of the configurable document, where each predefined version includes a different subset from the collection of subsets, as shown by block 412.

In an exemplary embodiment, the configurable document may correspond to a general concept, and each predefined version of the configurable document may be a particular arrangement of the configurable document that corresponds to a more refined version of the general concept. For example, a given configurable document may correspond to a certain document-category, and each predefined version of the configurable document may include a certain subset of the subparts that corresponds to a specific document-type within the document-category. As a more specific example, a configurable document may correspond to a certain medical issue, and the configurable document's collection of subparts may include information chunks related to the medical issue. Accordingly, each predefined version of the configurable document may include a subset of the collection of information chunks that corresponds to specific treatment of the medical issue. Many other examples are also possible.

In a further aspect, an exemplary embodiment may allow a user to label or name one or more of the predefined versions of a configurable document. For example, a computing device may receive a version-creation instruction that indicates to create a named version of the configurable document. The version-creation instruction may indicate: (a) a name for the version and/or (b) a particular arrangement of the configurable document. The arrangement may be indicated by, for example, (i) an indication of one or more selected subparts of the configurable document and/or (ii) for each selected subpart, an indication of a selected dimension of the subpart. The computing device may then create and store the named version of configurable document, so that the particular arrangement can be quickly and easily retrieved at a later time.

In some embodiments, a subpart of a configurable document may itself include a subpart or subparts. For clarity, a subpart of a subpart may be referred to as a "sub-subpart." Further, a sub-subpart may itself have a number of dimensions and/or may have its own subparts (e.g., "sub-sub-subparts"). Yet further, a sub-sub-subpart may also have its own subpart, and so on; such that it is possible for a multi-dimensional configurable document to have any number of dimensions.

In other words, if a configurable document has subparts that do not have sub-subparts (i.e., each subpart has a number of defined dimensions), then the configurable document may be said to be two-dimensional, as the particular subparts and the dimensions of those subparts can be manipulated. And if a configurable document has at least one subpart that includes sub-subparts, then the configurable document may be said to be two-dimensional, as the particular subparts, the sub-subparts of the subparts, and the dimensions of the sub-subparts can all be manipulated. Thus it can be seen that a configurable document have any number of dimensions.

In some embodiments, however, the number of dimensions may be limited by design. For example, some embodiments may only allow for creation of a three-dimensional configurable document (e.g., by allowing the user to include sub-subparts of a subpart, but not allowing for further subparts beyond the sub-subparts). Other examples are also possible.

Methods for Creating a Custom Version of a Configurable Document

As noted above, an exemplary embodiment may further involve an editing interface that allows user to create a version of a predefined configurable document by, for example, selecting which subparts to include and/or indicating which dimensions of the selected subparts to include in the version. Such an interface may be used to create a version of a predefined configurable document that was created using a method such as method 400, for example.

Figure 5:
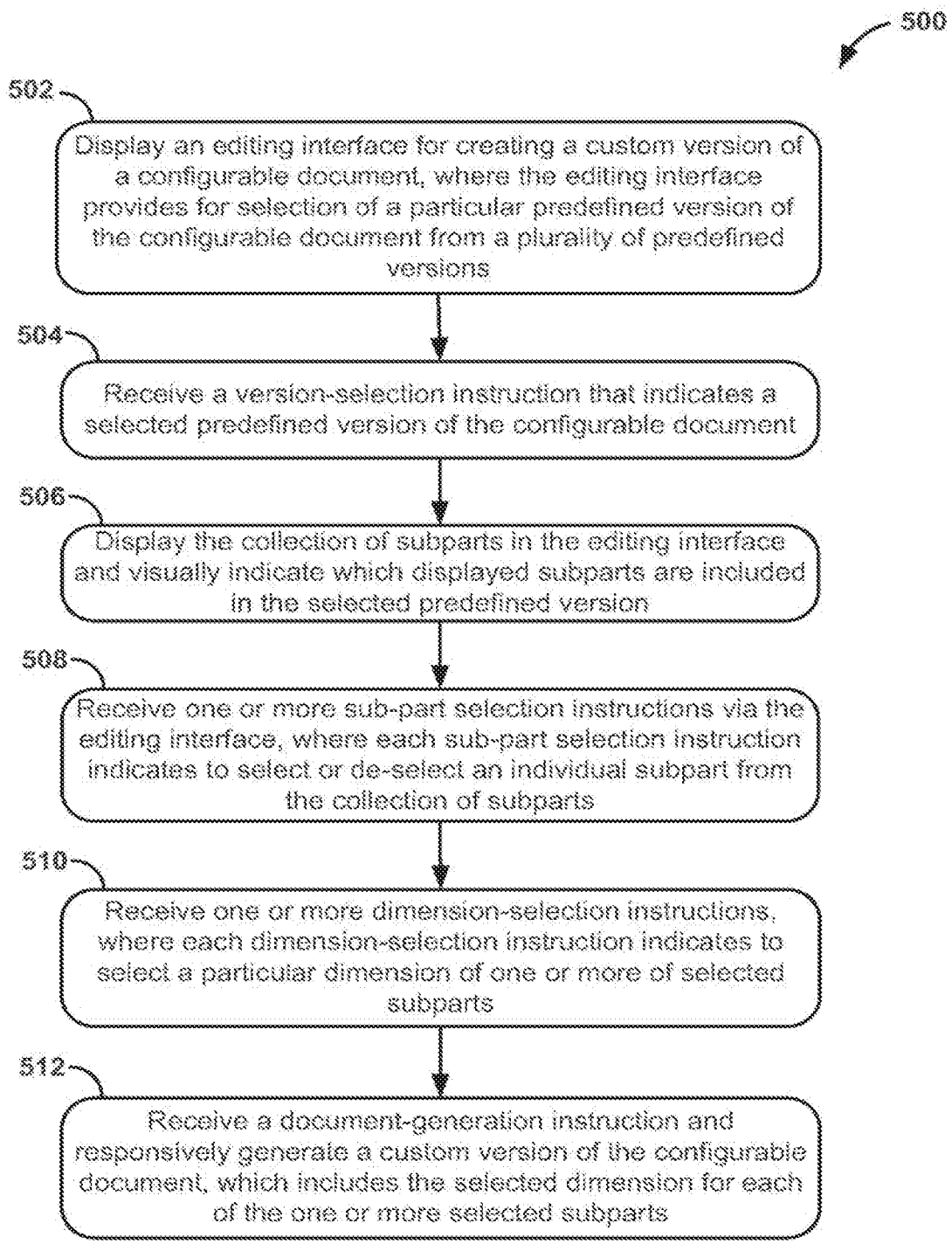
FIG. 5 is a flow chart illustrating another method, according to an exemplary embodiment.

FIG. 5 is a flow chart illustrating another method 500, according to an exemplary embodiment. Method 500 may be implemented by a computing device to provide an editing interface for creating a version of a configurable document, selecting particular subparts and particular dimensions of these subparts to include the version, and generating and storing the version of the configurable document based upon these selections.

More specifically, method 500 involves a computing device causing a graphic display to display an editing interface for creating a custom version of a configurable document, where the editing interface provides for selection of a particular predefined version of the configurable document from a plurality of predefined versions, as shown by block 502. The computing device then receives a version-selection instruction that indicates a selected predefined version of the configurable document, as shown by block 504. In response to the version-selection instruction, the computing device may cause the graphic display to display the collection of subparts in the editing interface, and to visually indicate which displayed subparts are included in the selected predefined version, as shown by block 506. Further, the selected predefined version may be displayed according to a default dimension.

At this point, the editing interface may allow the user to output the predefined version in the default dimension (e.g., by printing or generating a PDF file of predefined version in the default dimension). The editing interface may also allow the user to switch to a different dimension and then output the predefined version in the different dimension. However, the user may also customize the predefined version by, for example, selecting and/or deselecting certain subparts, and/or by changing the dimension for some or all of the subparts.

Accordingly, method 500 may further involve the computing device receiving one or more sub-part selection instructions via the editing interface, where each sub-part selection instruction indicates to select or de-select an individual subpart from the collection of subparts, as shown by block 508. The computing device may also receive one or more dimension-selection instructions, where each dimension-selection instruction indicates to select a particular dimension of one or more of selected subparts, as shown by block 510. The computing device may then receive a document-generation instruction and responsively generate a custom version of the configurable document, which includes the selected dimension for each of the one or more selected subparts, as shown by block 512.

In a further aspect, while methods 400 and 500 are described independently, it should be understood that the methods may be implemented in a common software program that allows a user to author, edit, finalize, and/or output a multi-dimensional configurable document. Accordingly, methods 400 and 500 may involve the same editing interface. Alternatively, it is possible that methods 400 and 500 may be implemented in different software programs, and may provide different editing interfaces.

Exemplary Editing Interface

In an exemplary embodiment, an editing interface may include two or more different screens that allow a user to: (a) compose and/or author a configurable document via a method such as method 400, and (b) create a custom version or view of the configurable document via a method such as method 500. When a user composes a custom version or view of a document, this version may be flattened to be a "one-dimensional" document, so that it can be printed or saved in a certain file format (e.g., as a PDF document).

FIG. 6A is an illustration of a screen 600 from an editing interface in a medical application, according to an exemplary embodiment. In particular, screen 600 shows a list of predefined versions 602 of two different configurable documents related to a user search in search bar 604. As shown in list 602, three versions of a "Bee Sting" configurable document may be selected: a "No EpiPen" version, a "W/EpiPen+Skin Testing" version, and a "With EpiPen" version. Similarly, three versions of a "Bee Sting (Peds)" configurable document may be selected: a "No EpiPen" version, a "W/EpiPen+Skin Testing" version, and a "With EpiPen" version.

Figure 6B:
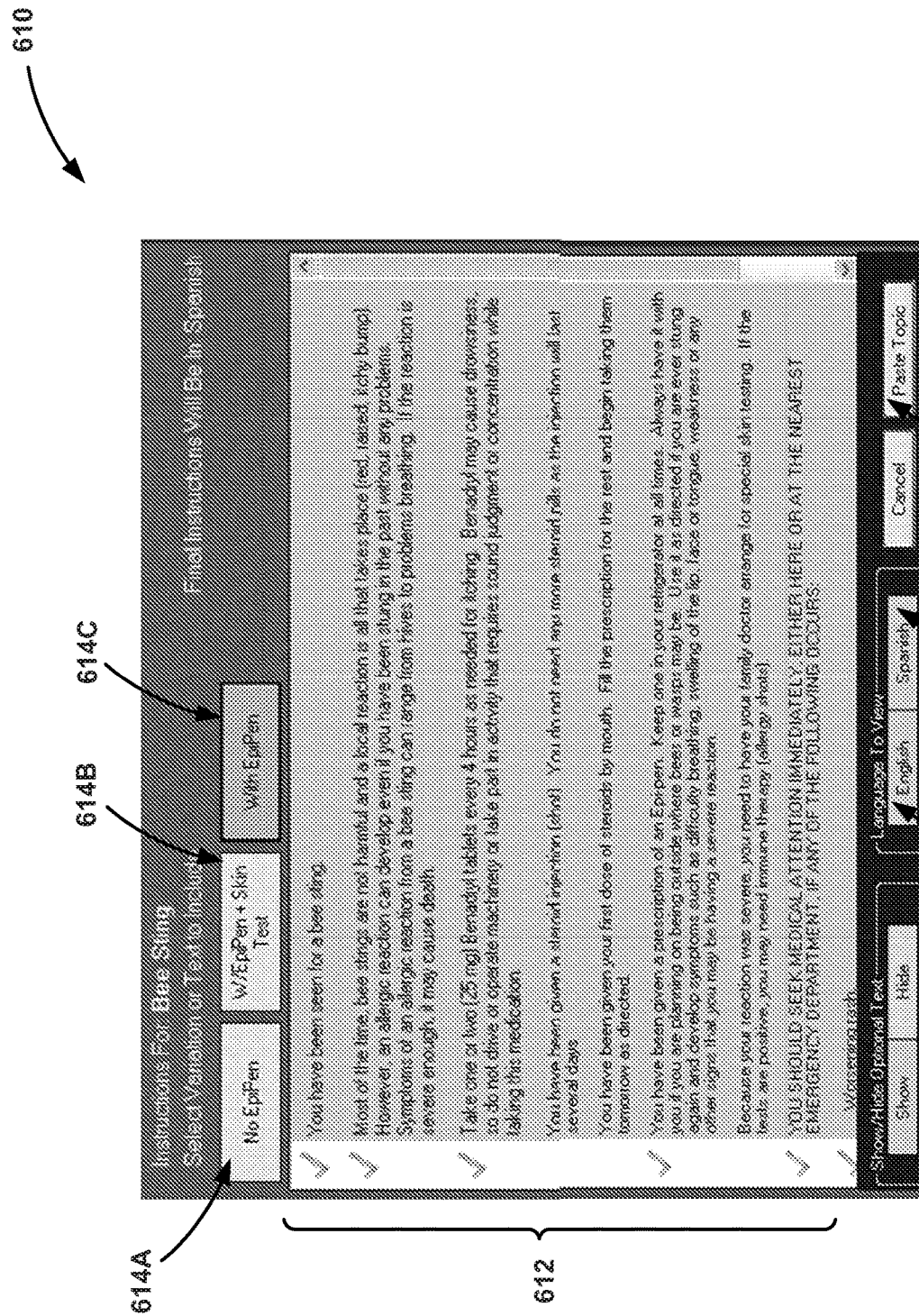
FIG. 6B is an illustration of another screen from an editing interface in a medical application, according to an exemplary embodiment

FIG. 6B is an illustration of another screen 610 from an editing interface in a medical application, according to an exemplary embodiment. In particular, screen 610 may be displayed when a given predefined version is selected from the list of predefined versions 602. In the illustrated example, the "With EpiPen" version of the "Bee Sting" configurable document was selected from list 602. As such, all the subparts 612 of the "Bee Sting" configurable document are displayed in screen 610. However, since the "With EpiPen" version was selected, a checkmark is displayed next to the subset of subparts 612 that are included in this version.

Note that while list 602 is described as having predefined versions of the selected configurable document, the interface may allow a user to select from other versions as well. For example, an editing interface may allow a user to select from a list that includes custom versions of a configurable document, in addition or in the alternative to the predefined versions. Other examples are also possible.

Further, screen 610 includes a button for each predefined version of the "Bee Sting" configurable document. Thus, screen 610 includes a "No EpiPen" button 614A, a "W/EpiPen+Skin Testing" button 614B, and a "With EpiPen" button 614C. Further, since the "With EpiPen" version was selected, the "With EpiPen" button 614C. However, screen 610 may allow a user to switch between the different versions of the "Bee Sting" configurable document by clicking the respective button.

In a further aspect, screen 610 may allow the user to select a dimension to view and/or a dimension to output. In the illustrated embodiment, each dimension corresponds to a different language. Accordingly, screen 610 includes a button 616A for "English" and a button 616B for "Spanish." Note that in an exemplary embodiment, the dimension that is being viewed may differ from the outputted dimension. For instance, as shown by screen 610, the final instructions will be in Spanish, even though the dimension being viewed is English.

Figure 6C:
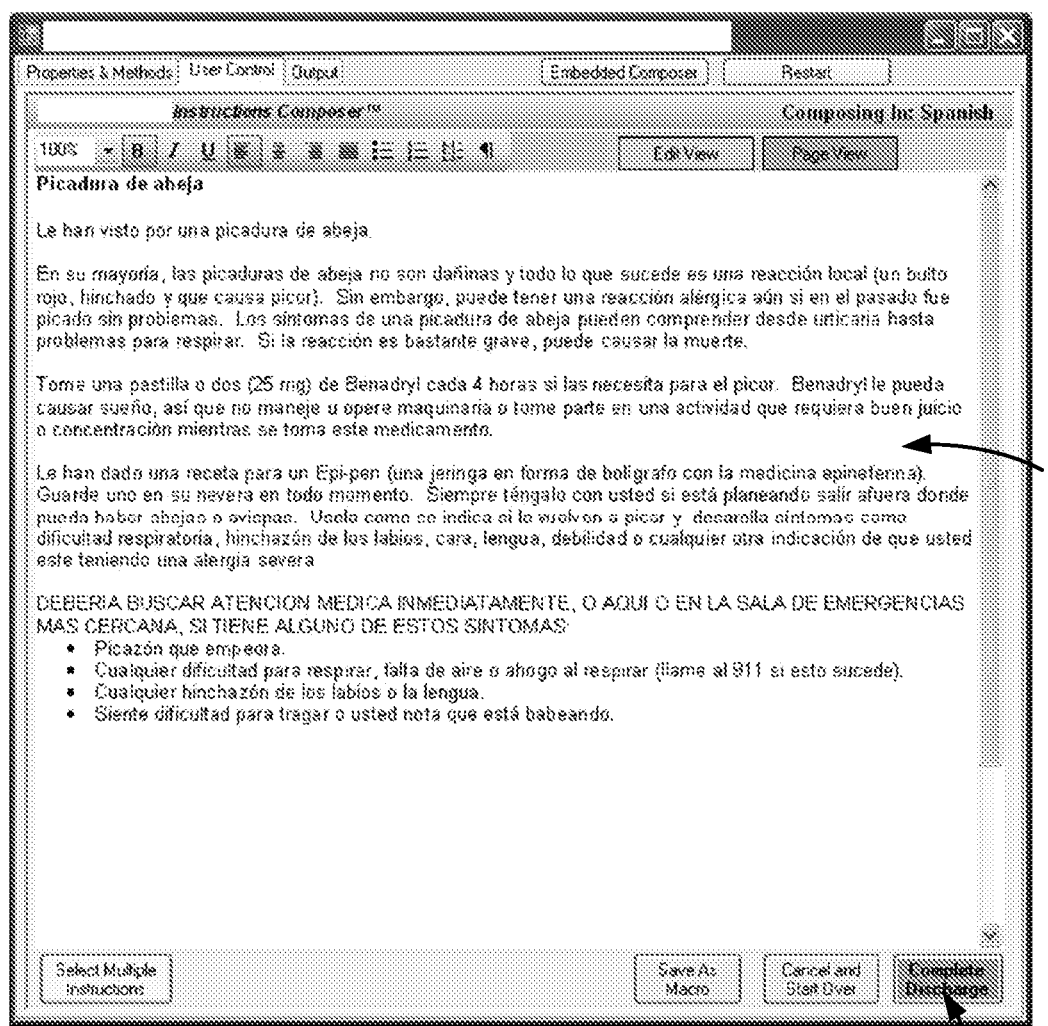
FIG. 6C is an illustration of another screen from an editing interface in a medical application, according to an exemplary embodiment

FIG. 6C is an illustration of another screen 620 from an editing interface in a medical application, according to an exemplary embodiment. In particular, screen 620 illustrates a one-dimensional document that has been generated from an arrangement of the configurable document that was created using a screen such as screen 610. For instance, when a user clicks on the "Paste Topic" button 618 of screen 610, the subparts that are selected on screen 610 may be flattened to create a one-dimensional document for display on screen 620.

More specifically, in the illustrated example, screen 620 includes a document-editing window 622, which is opened with a Spanish-language document that is composed from the Spanish dimension of the subparts that were selected in screen 610. Screen 620 may allow a user to output the one-dimensional document by, for example, clicking on the "Complete Discharge" button 624. This may result in a number of actions, such as printing the document, creating a file for the document, and/or e-mailing a file of the document, among others.

In a further aspect, the formatting of the one-dimensional document displayed in document-editing window 622 may be based on the subpart structure of the corresponding arrangement. For example, in the last paragraph shown in document-editing window 622, there is a text segment in capital letters, which is followed by four text segments that are formatted with bullet points. According to an exemplary embodiment, the bullet-point formatting may be implemented because each text segment that is formatted with a bullet point is a sub-subpart of the subpart corresponding to the text segment that is capitalized. It should be understood that this is but one example of formatting based on subpart structure, and that other examples are also possible. In general the formatting of a subpart in a one-dimensional version of a document, such as that shown in FIG. 6C, may be based on predefined formatting associated with the subpart itself and/or the relationship between the subparts that are included in a particular version of the configurable document.

As such, an exemplary method may further involve converting a multi-dimensional view or version of a configurable document to a one dimensional document (e.g., converting a view such as that shown on screen 610 or screen 710 to a one-dimensional, editable, document, such as that shown on screen 620). When this is done, the system may dynamically determine how subparts are arranged based on which subparts are selected and/or the relationship between the selected subparts.

Figure 7A:
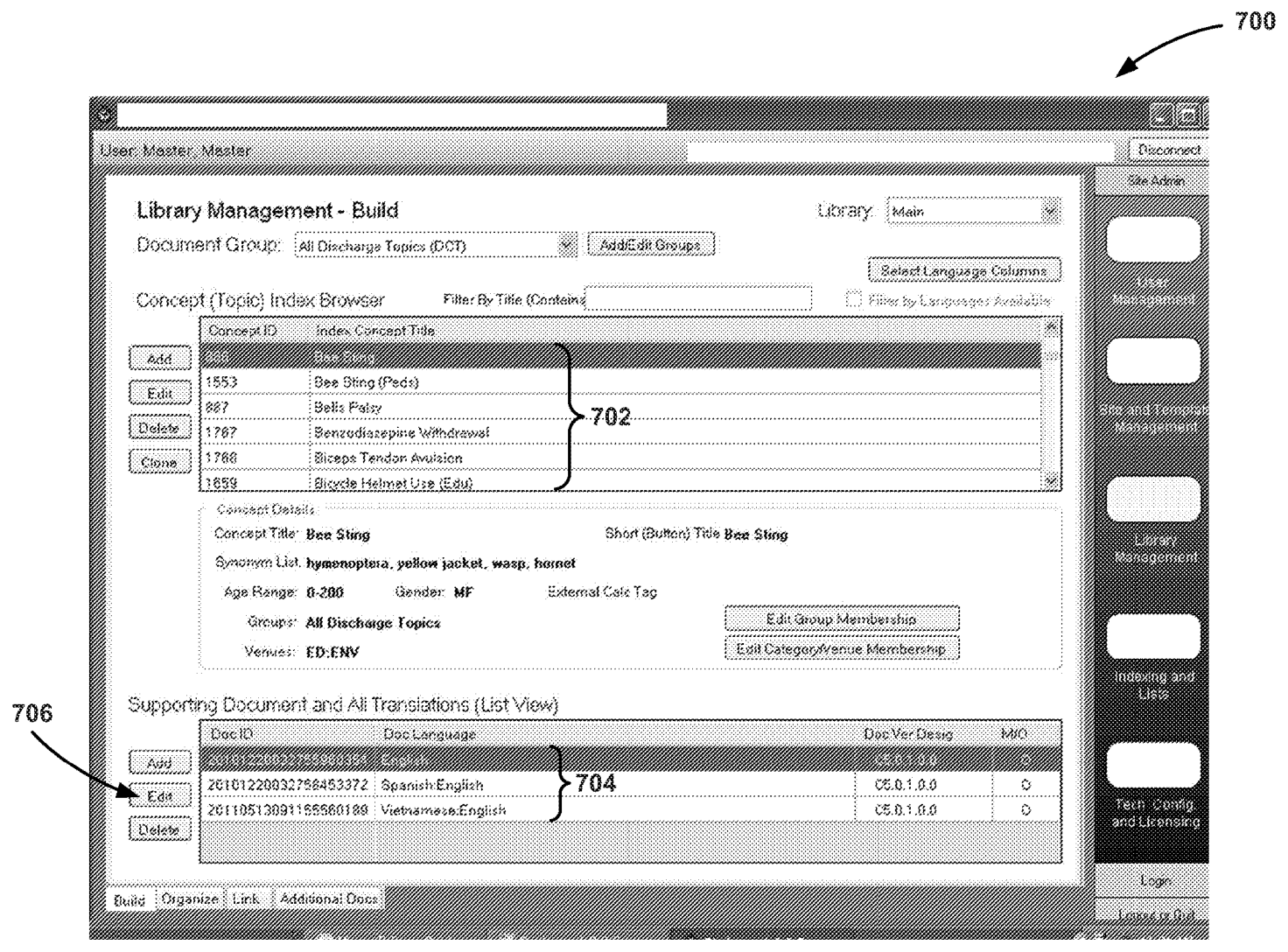

FIG. 7A is an illustration of another screen 700 from an editing interface in a medical application, according to an exemplary embodiment. In particular, screen 700 shows a list of configurable documents 702, which are referred to in the illustrated embodiment as "Topics." As shown in list 702, a user has selected a "Bee Sting" configurable document from a list of configurable documents that includes a "Bee Sting (Peds)" configurable document, a "Bells Palsy" configurable document, a "Benzodiazepine Withdrawal" configurable document, a "Biceps Tendon Avulsion" configurable document, a "Bicycle Helmet Use (Edu)" configurable document, as well as other configurable documents.

Screen 700 also includes a list of dimensions 704, which includes the various dimensions that are available to view for the configurable document that is selected from list 702. In the illustrated example, three views are available for the selected "Bee Sting" configurable document: a view of an English dimension, a dual view of both the Spanish and English dimensions, and another dual view of both the Vietnamese and English dimensions.

Figure 7B:
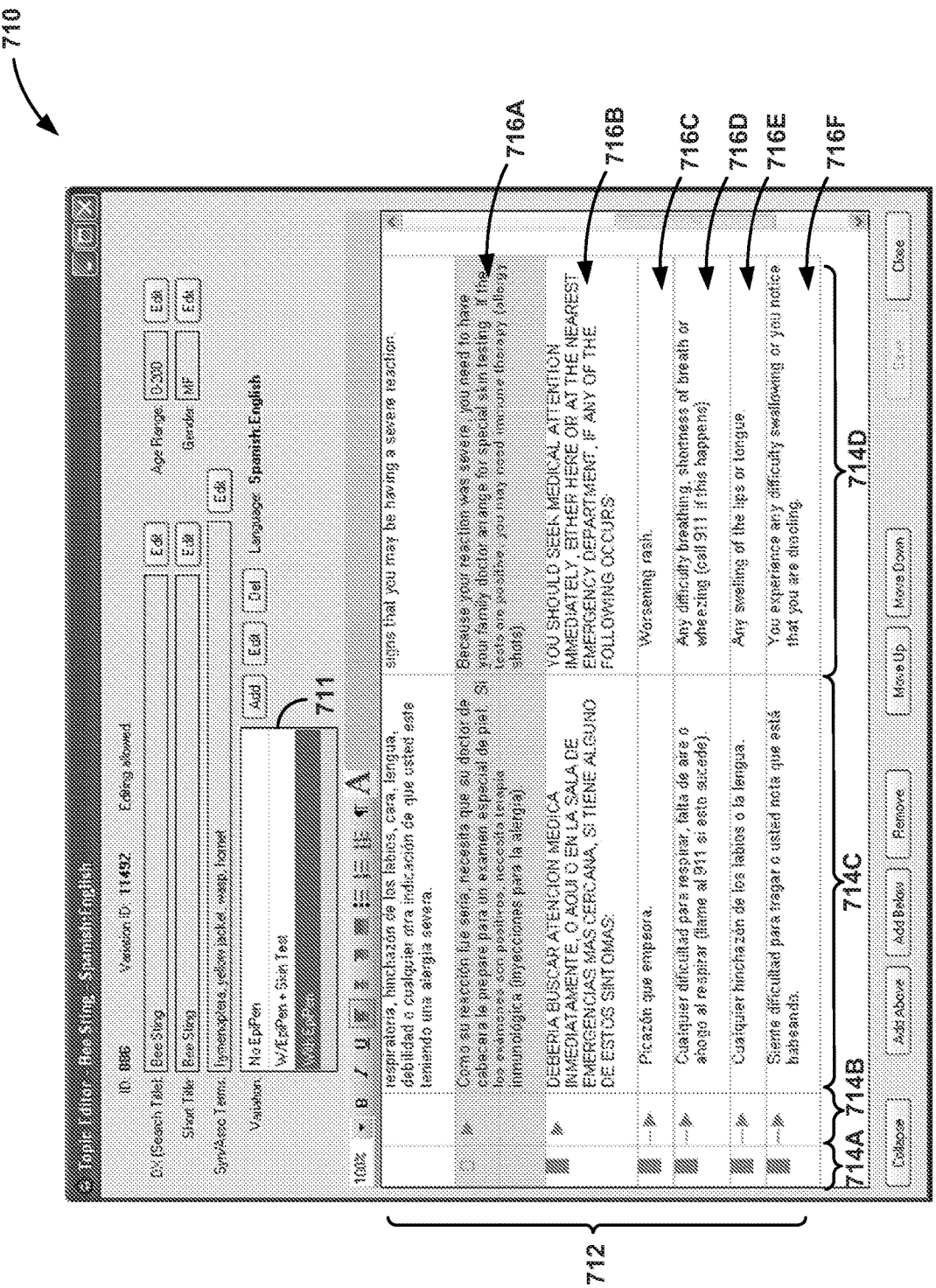
FIG. 7B is an illustration of another screen from an editing interface in a medical application, according to an exemplary embodiment.

FIG. 7B is an illustration of another screen 710 from an editing interface in a medical application, according to an exemplary embodiment. In particular, screen 710, allows a user to edit a configurable document by, for example, switching between various predefined versions of a configurable document, and selecting, deselecting, and/or arranging subparts of the configurable document to create custom views of the configurable document. As such, screen 710 may be displayed when a user selects the dual view of both the Vietnamese and English dimensions from list 704 and the "Bee Sting" configurable document on screen 700, and then clicks the "Edit" button 706 on screen 700.

Note that in the example illustrated by FIGS. 7A and 7B, configurable documents take the form of "Topics." Thus, the term "topic" and the term "configurable document" should be understood to be interchangeable. Accordingly, screen 710 may be referred to as a "Topic Editor."

Also note that in the example illustrated by FIGS. 7A and 7B, the predefined versions of a configurable document are referred to as "variations" of the configurable document. Thus, the term "version" and the term "variation" should be understood to be interchangeable. Accordingly, screen 710 also includes a variation-selection window 711, which allows the user to select and switch between the various predefined variations of the selected topic (e.g., of the selected configurable document). As shown, variation-selection window 711 includes the three predefined variations of the "Bee Sting" topic; the "No EpiPen" variation, the "W/EpiPen+Skin Test" variation, and the "With EpiPen" variation (which is the currently selected variation in FIG. 7B).

As further shown in FIG. 7B, screen 710 includes a table 712 for arranging the subparts. Each row 716A to 716F in table 712 corresponds to a certain subpart of the selected topic. Further, table 712 is an example of a "split view" of a configurable document, which allows a user to concurrently view multiple dimensions of each subpart of a configurable document. In the split view, column 714C shows a "Spanish" dimension of the "Bee Sting" configurable document and column 714D shows an "English" dimension of the "Bee Sting" configurable document. As such, the individual cells in column 714C include the "Spanish" dimension of the subpart corresponding to the particular row in which the cell is located. Likewise, the individual cells in column 714D include the "English" dimension of the subpart corresponding to the particular row in which the cell is located. Further, while the illustrated example shows two dimensions of the "Bee Sting" configurable document (e.g., "English" and "Spanish"), more than two dimensions may also be shown in a split view.

Furthermore, table 712 may allow a user to edit the text in a given dimension of a given subpart (or edit whatever other modality of data is included in a dimension of the subpart). For instance, the user may click on a cell in column 714C or 714D to edit the text in the Spanish or English dimension, respectively. In a further aspect, when a subpart is edited in one dimension, a visual cue may be displayed to the user that indicates a possibly inconsistency between dimensions of the subpart. Accordingly, the user may choose to update the other dimension or dimensions of the subpart to maintain consistency between the dimensions. Alternatively, it is possible that an exemplary system may update other dimensions automatically to maintain consistency between dimensions.

Table 712 includes a subpart-selection column 714A, which allows for the selection or de-selection of individual subparts of the topic. In the illustrated screen, this may be accomplished by a rectangular icon in each cell of column 714A, which the user can click on to select or de-select the subpart in the particular row in which the cell is located, and which is filled in when a subpart is selected. For instance, on screen 710, the subparts corresponding to rows 716B to 716F are selected, while the subpart corresponding to row 716A is not selected.

In an exemplary embodiment, when a predefined variation of a topic is first selected in variation-selection window 711, table 712 may display all the subparts of the topic. However, table 712 may visually indicate the subset of subparts that are included in the selected variation. For example, the respective rectangular icon in column 714A may be filled in for only those subparts that are included in the selected variation. Alternatively, when a predefined variation of a topic is first selected, table 712 may only display those subparts that are included in the selected variation.

After the subparts of the selected variation are automatically selected, screen 710 may allow a user to create a custom view of the document. For example, the rectangular icons in column 714A may allow a user to select and/or de-select subparts as they choose. Further, the user may click on a cell in column 714C or 714D to edit the text in a given dimension of a given subpart. After using such functions to create a custom view, screen 710 may further allow the custom view to be saved as a custom variation (e.g., a custom version) of the configurable document, so it can be retrieved at a later time.

In a further aspect, table 712 also includes a subpart-level column 714B, which allows a user to create a hierarchy of subparts. In the illustrated example, each cell in column 714B indicates a subpart level of the subpart in the row in which the cell is located. For example, the cells (714B, 716A) and (714B, 716B) include a basic arrow icon, which indicates that these are first-level subparts. The cells (714B, 716C) through (714B, 716F), on the other hand, all include an arrow icon with a stem, which indicates that these are second-level subparts (i.e., sub-subparts). In particular, the arrangement shown in table 712 may indicate that rows 716C to 716F are all subparts of the subpart in the immediately preceding row 716B.

The subpart-level of each subpart may be specified as part of a predefined version of a configurable document. Accordingly, when a predefined variation of a topic is first selected in variation-selection window 711, table 712 may set each subpart in the configurable document to predefined or default subpart-level. However, screen 710 may also allow a user to change the subpart-level of a given subpart. For instance, in the illustrated example, only two subpart levels are possible. Accordingly, a user may click on the icon in a cell of column 714B to change the subpart level of the subpart in the row in which the cell is located.

It should be understood that screen 710 illustrates but one of many ways in which an editing interface may allow for the subpart-level to be adjusted. Further, as more than two subpart-levels are possible, other embodiment may provide a interface via switch a user can select between more than two subpart-levels for a given subpart.

Further, if a given subpart is selected or de-selected, any subparts of the given subpart may likewise be selected or de-selected. However, after sub-subparts are selected or de-selected in this manner, screen 710 may further allow a user to customize the view by individually selecting sub-subparts. For example, if the subpart in column 716B is selected, its sub-subparts in columns 716C to 716F may be automatically selected. However, the user may be able to de-select individual sub-subparts by, for example, clicking on the sub-subparts icon in subpart-selection column 714A. Other examples and variations on this example are also possible.

From the foregoing description, one ordinarily skilled in the art can easily ascertain the essential characteristics of this invention and, without departing from the spirit and scope thereof, make various changes and modifications to the invention to adapt it to various usages and conditions.

I claim:

1. A computing system comprising:
 a database storing: (i) a plurality of document subparts related to a medical topic, wherein each of the document subparts is available in two or more languages, (ii) a first pre-defined subset of the document subparts representing a first combination of information concerning the medical topic, and (iii) a second pre-defined subset of the document subparts representing a second combination of information concerning the medical topic, wherein the first combination is different from the second combination; and a computing device including a processor configured to:

provide, for display on a graphical user interface, (i) a textual representation of the document subparts, (ii) a plurality of binary indicators, each associated with one of the document subparts and signifying whether the associated document subpart is selected, wherein an initial arrangement of the binary indicators signifies that only the first pre-defined subset of the document subparts are selected, (iii) subset controls indicating that the first pre-defined subset of the document subparts is selected and that the second pre-defined subset of the document subparts is not selected, and (iv) language controls indicating a selected language of the two or more languages, and (v) a document generation control;

in response to selection of one of the subset controls by way of the graphical user interface, provide, for display on the graphical user interface, (i) the subset controls indicating that the second pre-defined subset of the document subparts is selected and that the first pre-defined subset of the document subparts is not selected, and (ii) an update to the binary indicators so that they signify that only the second pre-defined subset of the document subparts are selected;

in response to selection of one of the language controls by way of the graphical user interface, provide, for display on the graphical user interface, an update to the language controls to indicate the selected language to be a different language of the two or more languages; and in response to selection of the document generation control by way of the graphical user interface, generate a document in the selected language and including only the document subparts signified as selected by the binary indicators.

2. The computing system of claim 1, wherein the processor is further configured to:

provide, for display on a previous graphical user interface, a list of selectable medical topics including the medical topic, wherein the list of selectable medical topics was generated as a search result, and wherein selection of the medical topic by way of the previous graphical user interface causes the graphical user interface to be provided.

3. The computing system of claim 1, wherein the selected language is different from a language of the two or more languages in which the textual representation of the document subparts is displayed.

4. The computing system of claim 1, wherein, prior to generating the document in the selected language, text of the document subparts is editable by way of the graphical user interface.

5. The computing system of claim 1, wherein, after generating the document in the selected language, the graphical user interface displays further controls for printing the document, storing the document in a file, and emailing the document.

6. The computing system of claim 1, wherein at least some of the document subparts signified as selected by the binary indicators contain sub-subparts, and wherein generating the document in the selected language comprises formatting the document subparts as text blocks and the sub-subparts in bulleted lists.

7. The computing system of claim 1, wherein the processor is further configured to:

provide, for display on a configuration graphical user interface, (i) a list of selectable medical topics including the medical topic indicated to be selected, (ii) a summary of the medical topic including a topic name, relevant symptoms, a relevant age range, and a relevant gender, and (iii) a list of selectable language versions of the first pre-defined subset of the document subparts.

8. The computing system of claim 7, wherein the configuration graphical user interface further includes: (i) topic editing controls for the list of selectable medical topics that allow addition of a new medical topic, editing of a selected medical topic, deletion of the selected medical topic, and copying of the selected medical topic, and (ii) language editing controls for the list of selectable language versions that allow addition of a new language version, editing one or more of the selectable language versions, and deletion of one or more of the selectable language versions.

9. The computing system of claim 8, wherein the processor is further configured to:

in response to selection to edit a first language version and a second language version of the selectable language versions, provide, for display on a second configuration graphical user interface, a table, wherein the table includes rows containing each of the document subparts in the first pre-defined subset thereof, and wherein the table includes a first column containing text of the document subparts in a first language and a second column containing text of the document subparts in a second language.

10. The computing system of claim 9, wherein the text in the table is editable and can be rearranged by way of the second configuration graphical user interface.

11. The computing system of claim 1, wherein languages of the document subparts are a first dimension of the document subparts and versions of the document subparts are a second dimension of the document subparts.

12. A computer-implemented method comprising:

storing, in a database, (i) a plurality of document subparts related to a medical topic, wherein each of the document subparts is available in two or more languages, (ii) a first pre-defined subset of the document subparts representing a first combination of information concerning the medical topic, and (iii) a second pre-defined subset of the document subparts representing a second combination of information concerning the medical topic, wherein the first combination is different from the second combination providing, for display on a graphical user interface, (i) a textual representation of the document subparts, (ii) a plurality of binary indicators, each associated with one of the document subparts and signifying whether the associated document subpart is selected, wherein an initial arrangement of the binary indicators signifies that only the first pre-defined subset of the document subparts are selected, (iii) subset controls indicating that the first pre-defined subset of the document subparts is selected and that the second pre-defined subset of the document subparts is not selected, and (iv) language controls indicating a selected language of the two or more languages, and (v) a document generation control;

in response to selection of one of the subset controls by way of the graphical user interface, providing, for display on the graphical user interface, (i) the subset controls indicating that the second pre-defined subset of the document subparts is selected and that the first pre-defined subset of the document subparts is not selected, and (ii) an update to the binary indicators so that they signify that only the second pre-defined subset of the document subparts are selected;

in response to selection of one of the language controls by way of the graphical user interface, providing, for display on the graphical user interface, an update to the language controls to indicate the selected language to be a different language of the two or more languages; and in response to selection of the document generation control by way of the graphical user interface, generating a document in the selected language and including only the document subparts signified as selected by the binary indicators.

13. The computer-implemented method of claim 12, further comprising:
providing, for display on a previous graphical user interface, a list of selectable medical topics including the medical topic, wherein the list of selectable medical topics was generated as a search result, and wherein selection of the medical topic by way of the previous graphical user interface causes the graphical user interface to be provided.

14. The computer-implemented method of claim 12, wherein the selected language is different from a language of the two or more languages in which the textual representation of the document subparts is displayed.

15. The computer-implemented method of claim 12, further comprising:
providing, for display on a configuration graphical user interface, (i) a list of selectable medical topics including the medical topic indicated to be selected, (ii) a summary of the medical topic including a topic name, relevant symptoms, a relevant age range, and a relevant gender, and (iii) a list of selectable language versions of the first pre-defined subset of the document subparts.

16. The computer-implemented method of claim 15, wherein the configuration graphical user interface further includes: (i) topic editing controls for the list of selectable medical topics that allow addition of a new medical topic, editing of a selected medical topic, deletion of the selected medical topic, and copying of the selected medical topic, and (ii) language editing controls for the list of selectable language versions that allow addition of a new language version, editing one or more of the selectable language versions, and deletion of one or more of the selectable language versions.

17. The computer-implemented method of claim 16, further comprising:
in response to selection to edit a first language version and a second language version of the selectable language versions, provide, for display on a second configuration graphical user interface, a table, wherein the table includes rows containing each of the document subparts in the first pre-defined subset thereof, and wherein the table includes a first column containing text of the document subparts in a first language and a second column containing text of the document subparts in a second language.

18. A non-transitory computer-readable medium having instructions stored thereon that, when executed by a processor, causes a computing device to perform operations comprising: storing, in a database, (i) a plurality of document subparts related to a medical topic, wherein each of the document subparts is available in two or more languages, (ii) a first pre-defined subset of the document subparts representing a first combination of information concerning the medical topic, and (iii) a second pre-defined subset of the document subparts representing a second combination of information concerning the medical topic, wherein the first combination is different from the second combination providing, for display on a graphical user interface, (i) a textual representation of the document subparts, (ii) a plurality of binary indicators, each associated with one of the document subparts and signifying whether the associated document subpart is selected, wherein an initial arrangement of the binary indicators signifies that only the first pre-defined subset of the document subparts are selected, (iii) subset controls indicating that the first pre-defined subset of the document subparts is selected and that the second pre-defined subset of the document subparts is not selected, and (iv) language controls indicating a selected language of the two or more languages, and (v) a document generation control; in response to selection of one of the subset controls by way of the graphical user interface, providing, for display on the graphical user interface, (i) the subset controls indicating that the second pre-defined subset of the document subparts is selected and that the first pre-defined subset of the document subparts is not selected, and (ii) an update to the binary indicators so that they signify that only the second pre-defined subset of the document subparts are selected; in response to selection of one of the language controls by way of the graphical user interface, providing, for display on the graphical user interface, an update to the language controls to indicate the selected language to be a different language of the two or more languages; and in response to selection of the document generation control by way of the graphical user interface, generating a document in the selected language and including only the document subparts signified as selected by the binary indicators.

19. The non-transitory computer-readable medium of claim 18, the operations further comprising: providing, for display on a previous graphical user interface, a list of selectable medical topics including the medical topic, wherein the list of selectable medical topics was generated as a search result, and wherein selection of the medical topic by way of the previous graphical user interface causes the graphical user interface to be provided.

20. The non-transitory computer-readable medium of claim 18, the operations further comprising: providing, for display on a configuration graphical user interface, (i) a list of selectable medical topics including the medical topic indicated to be selected, (ii) a summary of the medical topic including a topic name, relevant symptoms, a relevant age range, and a relevant gender, and (iii) a list of selectable language versions of the first pre-defined subset of the document subparts.

* * * * *